United States Patent
Echelard et al.

(12)

(10) Patent No.: US 6,210,736 B1
(45) Date of Patent: Apr. 3, 2001

(54) TRANSGENICALLY PRODUCED PROLACTIN

(75) Inventors: Yann Echelard, Brookline; Brian Wilburn, Boston, both of MA (US)

(73) Assignee: Genzyme Transgenics Corporation, Framingham, MA (US)

( * ) Notice: Subject to any disclaimer, the term of this patent is extended or adjusted under 35 U.S.C. 154(b) by 0 days.

(21) Appl. No.: 09/094,781

(22) Filed: Jun. 15, 1998

Related U.S. Application Data

(60) Provisional application No. 60/049,856, filed on Jun. 17, 1997.

(51) Int. Cl.⁷ .............................. A23C 1/187; C07K 14/00
(52) U.S. Cl. .......................... 426/580; 530/399; 530/397
(58) Field of Search .................................. 800/4; 530/412, 530/399, 397; 424/157.2, 157.1; 514/2; 426/580

(56) References Cited

U.S. PATENT DOCUMENTS

| | | | |
|---|---|---|---|
| 4,725,549 | 2/1988 | Cooke et al. | 435/243 |
| 4,873,316 | 10/1989 | Meade et al. | 530/412 |
| 5,082,779 | 1/1992 | Rottman et al. | 435/172.3 |
| 5,344,920 | * 9/1994 | Price | 530/416 |
| 5,843,705 | * 12/1998 | DiTullio et al. | 435/69.1 |

FOREIGN PATENT DOCUMENTS

WO 94/05782    3/1994  (WO).

OTHER PUBLICATIONS

Lewis et al., (1985) *Endocrinology*, 116:359–363.
Gordon et al., (1987) *Biotechnology*, 5:1183–1186.
Price AE et al. Endocrinology 136:4827–4833. 1995.*
Yoneda N et al. European Journal of Endocrinology 133:613–617. 1995.*
Crenshaw, E. et al, "Cell–Specific Expression of the Prolactin Gene in Transgenic Mice is Controlled by Synergistic Interactions Between Promoter and Enhancer Elements", *Genes & Development*, 3:959–972 (1989).
Groner, B. et al, "Prolactin–Medicated Gene Activation in Mammary Epithelial Cells", *Current Opinion in Genetic's Development* 5:587–594, (1995).
Rosochacki, S.J., Polymerase Chain Reaction Used for Synthesis of Prolactin Promoter and Identification of Transgene in Animals, 24th Conference of ISAG, abstract E56, Dec. 1994.
Wilburn B., et al "High Level Expression of Recombinant Human Prolactin in the Milk of Transgenic Mice" *Theriogenology*, 47(1):219, (1997).

* cited by examiner

Primary Examiner—Karen M. Hauda
Assistant Examiner—Ram R. Shukla
(74) Attorney, Agent, or Firm—Fish & Richardson P.C.

(57) ABSTRACT

Transgenically produced prolactin and methods of making and using transgenically produced prolactin are disclosed.

6 Claims, No Drawings

TRANSGENICALLY PRODUCED PROLACTIN

This application claims the benefit of a previously filed Provisional Application No. 60/049,856 and PCT/US97/10489, both filed Jun. 17, 1997, which are hereby incorporated by reference.

The invention relates to transgenic prolactin, and methods of making and using transgenic prolactin.

BACKGROUND OF THE INVENTION

A growing number of recombinant proteins are being developed for therapeutic, diagnostic, agricultural, veterinary, nutritional and other applications; however, many of these proteins may be difficult or expensive to produce in a functional form in the substantial quantities using conventional methods.

Conventional methods often involve inserting the gene responsible for the production of a particular protein into host cells such as bacteria, yeast, or mammalian cells. The cells are grown in culture medium and the desired protein is recovered from the cells or the culture medium. Traditional bacteria or yeast systems are sometimes unable to produce a complex protein in finctional form. While some mammalian cells can reproduce complex proteins, they are often difficult and expensive to grow, and produce only protein in relatively low amounts. In addition, non-secreted proteins are relatively difficult to purify from procaryotic or mammalian cells, as they are often not secreted into the culture medium.

SUMMARY OF THE INVENTION

In general, the invention features, a transgenically produced preparation of prolactin, preferably human prolactin.

The transgenically produced prolactin is produced in a transgenic organism, i.e., a transgenic plant or animal. Preferred tralsgenic animals include: mammals; birds; reptiles; and amphibians. Suitable mammals include: ruminants; ungulates; domesticated mammals; and dairy animals. Particularly preferred animals include: goats, sheep, camels, cows, pigs, horses, oxen, and llamas. Suitable birds include chickens, geese, and turkeys. Where the transgenic protein is secreted into the milk of a transgenic animal, the animal should be able to produce at least 1, and more preferably at least 10, or 100, liters of milk per year.

In preferred embodiments, less than 50%, 40%, 30%, 25%, 20%, 15%, 10%, 5%, 2.5%, or 1% of the prolactin molecules in a transgenically made preparation, preferably as it is made in the transgenic organism, are glycosylated.

In preferred embodiments, the transgenically produced prolactin preparation, preferably as it is made in the transgenic organism, is less than 50%, 40%, 30%, 20%, 10%, or 5%, glycosylated (in terms of the number of molecules in a preparation which are glycosylated, or in terms of the total contribution of sugar to the molecular weight in a preparation) AS compared to the glycosylation of prolactin as it is found or as it is isolated from naturally occurring nontransgenic source, or as it is isolated from recombinantly produced prolactin in cell culture.

In preferred embodiments the transgenic preparation, preferably as it is made in the transgenic organism, includes glycosylated and non-glycosylated forms, and some or all of the glycosylated forms are removed, e.g., from a body fluid, e.g., milk, e.g., by standard protein separation methods.

In preferred embodiments, the transgenically produced prolactin is made in a mammary gland of the transgenic mammal, e.g., a ruminant, e.g., a goat.

In preferred embodiments, the transgenically produced prolactin is secreted into the milk of the transgenic mammal, e.g., a ruminant, e.g., a goat.

In preferred embodiments, the transgenically produced prolactin is made under the control of a mammary gland specific promoter, e.g., a milk specific promoter, e.g., a milk serum protein or casein promoter. The milk specific promoter can is a casein promoter, beta lactoglobulin promoter, whey acid protein promoter, or lactalbumin promoter.

In preferred embodiments, the prolactin is made under the control of a bladder, or egg specific promoter and prolactin is secreted into the urine or into an egg.

In preferred embodiments, the transgenically produced prolactin preparation differs in average molecular weight, activity, clearance time, or resistance to proteolytic degradation from non-transgenic forms.

In preferred embodiments, the glycosylation of the transgenically produced prolactin preparation differs from prolactin as it is found or as it is isolated from recombinantly produced prolactin in cell culture, or transgenic prolactin produced in mouse.

In preferred embodiments, the transgenically produced prolactin is expressed from a transgenic organism and the glycosylation of the transgenically produced prolactin preparation differs from the glycosylation of prolactin as it is found or as it is isolated from a bacterial cell, a yeast cell, an insect cell, a cultured mammalian cell, e.g., a CHO, COS, or HeLa cell. For example, it is different from a protein made by a cultured mammalian cell which has inserted into it a nucleic acid which encodes or directs the expression of prolactin.

In preferred embodiments, the prolactin is expressed from a transgenic mammal other than a rodent, e.g., mouse. For example, the prolactin is expressed from a goat, and the glycosylation of the transgenically produced prolactin differs from the glycosylation of prolactin as it is found or as it is isolated from a transgenic rodent which has inserted into it a nucleic acid which encodes or directs the expression of prolactin.

In preferred embodiments, the electrophoretic mobility of the prolactin preparation, e.g., as determined by SDS-PAGE, is different from the electrophoretic mobility of a naturally occurring human prolactin; the electrophoretic mobility of the preparation is different from the electrophoretic mobility of a recombinantly produced human prolactin produced in mammalian cells, e.g., CHO, COS, or HeLa cells, or procaryotic cells, e.g., bacteria, or yeast, or insect cells.

In preferred embodiments, the prolactin differs by at least one amino acid residue from a naturally occurring human prolactin; the prolactin differs by at least one amino acid residue from a recombinantly produced human prolactin produced in mammalian cells, e.g., CHO, COS, or HeLa cells, procaryotic cells, e.g., bacteria, or yeast, or insect cells.

In preferred embodiments, the prolactin the amino acid sequence is that of mammalian or primate, preferably human, prolactin.

In preferred embodiments, the preparation includes at least 1, 10, or 100 milligrams of prolactin. In preferred embodiments, the preparation includes at least 1, 10, or 100 grams of prolactin.

In preferred embodiments, the preparation includes at least 1, 10, 100, or 500 milligrams per milliliter of prolactin.

In another aspect, the invention features, an isolated nucleic acid molecule including a prolactin protein-coding sequence operatively linked to a tissue specific promoter, e.g., a mammary gland specific promoter sequence that results in the secretion of the protein in the milk of a transgenic mammal.

In preferred embodiments, the promoter is a milk specific promoter, e.g., a milk serum protein or casein promoter. The milk specific promoter can is a casein promoter, beta lactoglobulin promoter, whey acid protein promoter, or lactalbumin promoter.

In preferred embodiments, the promoter is a bladder, or egg specific promoter and prolactin is secreted into the urine or into an egg.

In preferred embodiments, the prolactin the amino acid sequence is that of mammalian or primate, preferably human, prolactin.

In another aspect, the invention features, a method of making transgenic prolactin or a preparation of transgenic prolactin. The method includes:

providing a transgenic organism, i.e., a transgenic animal or plant, which includes a transgene which directs the expression of prolactin, preferably human prolactin;

allowing the transgene to be expressed; and recovering transgenically produced prolactin or a preparation of transgenically produced prolactin, from the organism or from a product produced by the organism, e.g., milk, seeds, hair, blood, eggs, or urine.

In preferred embodiments, the method further includes:

inserting a nucleic acid which directs the expression of prolactin into a cell and allowing the cell to give rise to a transgenic organism;

Preferred transgenic animals include: mammals; birds; reptiles; and amphibians. Suitable mammals include: ruminants; ungulates; domesticated mammals; and dairy animals. Particularly preferred animals include: goats, sheep, camels, cows, pigs, horses, oxen, and llamas. Suitable birds include chickens, geese, and turkeys. Where the transgenic protein is secreted into the milk of a transgenic animal, the animal should be able to produce at least 1, and more preferably at least 10, or 100, liters of milk per year.

In preferred embodiments, less than 50%, 40%, 30%, 25%, 20%, 15%, 10%, 5%, 2.5%, or 1% of the prolactin molecules in a transgenically made preparation, preferably as it is made in the transgenic organism, are glycosylated.

In preferred embodiments, the transgenically produced prolactin preparation, preferably as it is made in the transgenic organism, is less than 50%, 40%, 30%, 20%, 10%, or 5%, glycosylated (in terms of the number of molecules in a preparation which are glycosylated, or in terms of the total contribution of sugar to the molecular weight in a preparation) as compared to the glycosylation of prolactin as it is found or as it is isolated from naturally occurring nontransgenic source, or as it is isolated from recombinantly produced prolactin in cell culture.

In preferred embodiments the transgenic preparation, preferably as it is made in the transgenic organism, includes glycosylated and non-glycosylated forms, and some or all of the glycosylated forms are removed, e.g., from a body fluid, e.g., milk, e.g., by standard protein separation methods.

In preferred embodiments, the transgenically produced prolactin is made in a mammary gland of the transgenic mammal, e.g., a ruminant, e.g., a goat.

In preferred embodiments, the transgenically produced prolactin is secreted into the milk of the transgenic mammal, e.g., a ruminant, e.g., a goat.

In preferred embodiments, the transgenically produced prolactin is made under the control of a mammary gland specific promoter, e.g., a milk specific promoter, e.g., a milk serum protein or casein promoter. The milk specific promoter can is a casein promoter, beta lactoglobulin promoter, whey acid protein promoter, or lactalbumin promoter.

In preferred embodiments, the prolactin is made under the control of a bladder, or egg specific promoter and prolactin is secreted into the urine or into an egg.

In preferred embodiments, the transgenically produced prolactin preparation differs in average molecular weight, activity, clearance time, or resistance to proteolytic degradation from non-transgenic forms.

In preferred embodiments, the glycosylation of the transgenically produced prolactin preparation differs from prolactin as it is found or as it is isolated from recombinantly produced prolactin in cell culture, or transgenic prolactin produced in mouse.

In preferred embodiments, the transgenically produced prolactin is expressed from a transgenic organism and the glycosylation of the transgenically produced prolactin preparation differs from the glycosylation of prolactin as it is found or as it is isolated from a bacterial cell, a yeast cell, an insect cell, a cultured mammalian cell, e.g., a CHO, COS, or HeLa cell. For example, it is different from a protein made by a cultured mammalian cell which has inserted into it a nucleic acid which encodes or directs the expression of prolactin.

In preferred embodiments, the prolactin is expressed from a transgenic mammal other than a rodent, e.g., mouse. For example, the prolactin is expressed from a goat, and the glycosylation of the transgenically produced prolactin differs from the glycosylation of prolactin as it is found or as it is isolated from a transgenic rodent which has inserted into it a nucleic acid which encodes or directs the expression of prolactin.

In preferred embodiments, the electrophoretic mobility of the prolactin preparation, e.g., as determined by SDS-PAGE, is different from the electrophoretic mobility of a naturally occurring human prolactin; the electrophoretic mobility of the preparation is different from the electrophoretic mobility of a recombinantly produced human prolactin produced in mammalian cells, e.g., CHO, COS, or HeLa cells, or procaryotic cells, e.g., bacteria, or yeast, or insect cells.

In preferred embodiments, the prolactin differs by at least one amino acid residue from a naturally occurring human prolactin; the prolactin differs by at least one amino acid residue from a recombinantly produced human prolactin produced in mammalian cells, e.g., CHO, COS, or HeLa cells, procaryotic cells, e.g., bacteria, or yeast, or insect cells.

In preferred embodiments, the prolactin the amino acid sequence is that of from mammalian or primate, preferably human, prolactin.

In preferred embodiments, the preparation includes at least 1, 10, or 100 milligrams of prolactin. In preferred embodiments, the preparation includes at least 1, 10, or 100 grams of prolactin.

In preferred embodiments, the preparation includes at least 1, 10, 100, or 500 milligrams per milliliter of prolactin.

In another aspect, the invention features, a method for providing a transgenic preparation which includes heterologous prolactin in the milk of a transgenic mammal including:

obtaining milk from a transgenic mammal having introduced into its germline a prolactin protein-coding sequence operatively linked to a promoter sequence that result in the expression of the protein-coding sequence in mammary gland epithelial cells, thereby secreting the prolactin in the milk of the mammal to provide the preparation.

Suitable mammals include: ruminants; ungulates; domesticated mammals; and dairy animals. Particularly preferred mammals include: goats, sheep, camels, cows, pigs, horses, oxen, and llamas. The transgenic mammal should be able to produce at least 1, and more preferably at least 10, or 100, liters of milk per year.

In preferred embodiments, less than 50%, 40%, 30%, 25%, 20%, 15%, 10%, 5%, 2.5%, or 1% of the prolactin molecules in a transgenically made preparation, preferably as it is made in the transgenic mammal, are glycosylated.

In preferred embodiments, the transgenically produced prolactin preparation, preferably as it is made in the transgenic mammal, is less than 50%, 40%, 30%, 25%, 20%, 15%, 10%, 5%, 2.5%, or 1%, glycosylated (in terms of the number of molecules in a preparation which are glycosylated, or in terms of the total contribution of sugar to the molecular weight in a preparation) as compared to the glycosylation of prolactin as it is found or as it is isolated from naturally occurring nontransgenic source, or as it is isolated from recombinantly produced prolactin in cell culture.

In preferred embodiments the taansgenic preparation, preferably as it is made in the transgenic mammal, includes glycosylated and non-glycosylated forms, and some or all of the glycosylated forms are removed from the milk, e.g., by standard protein separation methods.

In preferred embodiments, the transgenically produced prolactin is made in a mammary gland of the transgenic mammal, e.g., a ruminant, e.g., a goat.

In preferred embodiments, the transgenically produced prolactin is secreted into the milk of the transgenic mammal, e.g., a ruminant, e.g., a goat.

In preferred embodiments, the transgenically produced prolactin is made under the control of a mammary gland specific promoter, e.g., a milk specific promoter, e.g., a milk serum protein or casein promoter.. The milk specific promoter can is a casein promoter, beta lactoglobulin promoter, whey acid protein promoter, or lactalbumin promoter.

In preferred embodiments, the transgenically produced prolactin preparation differs in average molecular weight, activity, clearance time, or resistance to proteolytic degradation from non-transgenic forms.

In preferred embodiments, the glycosylation of the transgenically produced prolactin preparation differs from prolactin as it is found or as it is isolated from recombinantly produced prolactin in cell culture, or transgenic prolactin produced in mouse.

In preferred embodiments, the transgenically produced prolactin is expressed from a transgenic mammal and the glycosylation of the transgenically produced prolactin preparation differs from the glycosylation of prolactin as it is found or as it is isolated from a bacterial cell, a yeast cell, an insect cell, a cultured mammalian cell, e.g., a CHO, COS, or HeLa cell. For example, it is different from a protein made by a cultured mammalian cell which has inserted into it a nucleic acid which encodes or directs the expression of prolactin.

In preferred embodiments, the prolactin is expressed from a transgenic mammal other than a rodent, e.g., mouse. For example, the prolactin is expressed from a goat, and the glycosylation of the transgenically produced prolactin differs from the glycosylation of prolactin as it is found or as it is isolated from a transgenic rodent which has inserted into it a nucleic acid which encodes or directs the expression of prolactin.

In preferred embodiments, the electrophoretic mobility of the prolactin preparation, e.g., as determined by SDS-PAGE, is different from the electrophoretic mobility of a naturally occurring human prolactin; the electrophoretic mobility of the preparation is different from the electrophoretic mobility of a recombinantly produced human prolactin produced in mammalian cells, e.g., CHO, COS, or HeLa cells, or procaryotic cells, e.g., bacteria, or yeast, or insect cells.

In preferred embodiments, the prolactin differs by at least one amino acid residue from a naturally occurring human prolactin; the prolactin differs by at least one amino acid residue from a recombinantly produced human prolactin produced in mammalian cells, e.g., CHO, COS, or HeLa cells, procaryotic cells, e.g., bacteria, or yeast, or insect cells.

In preferred embodiments, the prolactin the amino acid sequence is that of from mammalian or primate, preferably human, prolactin.

In preferred embodiments, the milk includes at least 1, 10, 100, 500, 1,000, or 2,000 milligrams per milliliter, of prolactin.

In another aspect, the invention features, a transgenic organism, which expresses a transgenic prolactin, preferably human prolactin, and from which a transgenic preparation of prolactin can be obtained.

The transgenic organism is a transgenic plant or animal. Preferred transgenic animals include: mammals; birds; reptiles; and amphibians. Suitable mammals include: ruminants; ungulates; domesticated mammals; and dairy animals. Particularly preferred animals include: goats, sheep, camels, cows, pigs, horses, oxen, and llamas. Suitable birds include chickens, geese, and turkeys. Where the transgenic protein is secreted into the milk of a transgenic animal, the animal should be able to produce at least 1, and more preferably at least 10, or 100, liters of milk per year.

In preferred embodiments, less than 50%, 40%, 30%, 25%, 20%, 15%, 10%, 5%, 2.5%, or 1% of the prolactin molecules in a transgenically made preparation, preferably as it is made in the transgenic organism, are glycosylated.

In preferred embodiments, the transgenically produced prolactin preparation, preferably as it is made in the transgenic organism, is less than 50%, 40%, 30%, 25%, 20%, 15%, 10%, 5%, 2.5%, or 1%, glycosylated (in terms of the number of molecules in a preparation which are glycosylated, or in terms of the total contribution of sugar to the molecular weight in a preparation) as compared to the glycosylation of prolactin as it is found or as it is isolated from naturally occurring nontransgenic source, or as it is isolated from recombinantly produced prolactin in cell culture.

In preferred embodiments the transgenic preparation, preferably as it is made in the transgenic organism, includes glycosylated and non-glycosylated forms, and some or all of the glycosylated forms are removed, e.g., from a body fluid, e.g., milk, e.g., by standard protein separation methods.

In preferred embodiments, the transgenically produced prolactin is made in a mammary gland of the transgenic mammal, e.g., a ruminant, e.g., a goat.

In preferred embodiments, the transgenically produced prolactin is secreted into the milk of the transgenic mammal, e.g., a ruminant, e.g., a goat.

In preferred embodiments, the transgenically produced prolactin is made under the control of a mammary gland specific promoter, e.g., a milk specific promoter, e.g., a milk serum protein or casein promoter. The milk specific promoter can is a casein promoter, beta lactoglobulin promoter, whey acid protein promoter, or lactalbumin promoter.

In preferred embodiments, the prolactin is made under the control of a bladder, or egg specific promoter and is prolactin secreted into the urine or into an egg.

In preferred embodiments, the transgenically produced prolactin preparation differs in average molecular weight, activity, clearance time, or resistance to proteolytic degradation from non-transgenic forms.

In preferred embodiments, the glycosylation of the transgenically produced prolactin preparation differs from prolactin as it is found or as it is isolated from recombinantly produced prolactin in cell culture, or transgenic prolactin produced in mouse.

In preferred embodiments, the transgenically produced prolactin is expressed from a transgenic organism and the glycosylation of the transgenically produced prolactin preparation differs from the glycosylation of prolactin as it is found or as it is isolated from a bacterial cell, a yeast cell, an insect cell, a cultured mammalian cell, e.g., a CHO, COS, or HeLa cell. For example, it is different from a protein made by a cultured mammalian cell which has inserted into it a nucleic acid which encodes or directs the expression of prolactin.

In preferred embodiments, the prolactin is expressed from a transgenic mammal other than a rodent, e.g., mouse. For example, the prolactin is expressed from a goat, and the glycosylation of the transgenically produced prolactin differs from the glycosylation of prolactin as it is found or as it is isolated from a transgenic rodent which has inserted into it a nucleic acid which encodes or directs the expression of prolactin.

In preferred embodiments, the electrophoretic mobility of the prolactin preparation, e.g., as determined by SDS-PAGE, is different from the electrophoretic mobility of a naturally occurring human prolactin; the electrophoretic mobility of the preparation is different from the electrophoretic mobility of a recombinantly produced human prolactin produced in mammalian cells, e.g., CHO, COS, or HeLa cells, or procaryotic cells, e.g., bacteria, or yeast, or insect cells.

In preferred embodiments, the prolactin differs by at least one amino acid residue from a naturally occurring human prolactin; the prolactin differs by at least one amino acid residue from a recombinantly produced human prolactin produced in mammalian cells, e.g., CHO, COS, or HeLa cells, procaryotic cells, e.g., bacteria, or yeast, or insect cells.

In preferred embodiments, the prolactin the amino acid sequence is that of from mammalian or primate, preferably human, prolactin.

In preferred embodiments, the preparation includes at least 1, 10, or 100 milligrams of prolactin. In preferred embodiments, the preparation includes at least 1, 10, or 100 grams of prolactin.

In preferred embodiments, the preparation includes at least 1, 10, 100, or 500 milligrams per milliliter of prolactin.

In another aspect, the invention features, a pharmaceutical composition including a therapeutically effective amount of transgenic prolactin, or a transgenic preparation of prolactin, and a pharmaceutically acceptable carrier.

The transgenic prolactin or prolactin preparation can be made, e.g., by any method or organism described herein.

The transgenic prolactin or prolactin preparation can be, e.g., any described herein.

In another aspect, the invention features, a formulation, which includes a transgenically produced prolactin preparation, preferably human prolactin, and at least one other component, e.g. a nutritional component, other than prolactin.

In preferred embodiments, the formulation is a solid or liquid.

In preferred embodiments, the formulation further includes a liquid carrier.

In preferred embodiments, the nutritional component is: a protein, e.g., a milk protein; a vitamin, e.g., vitamin A, vitamin B, vitamin D; a carbohydrate; a mineral, e.g., calcium, phosphorous, iron.

The transgenic prolactin or prolactin preparation can be made, e.g., by any method or organism described herein.

The transgenic prolactin or prolactin preparation can be, e.g., any described herein.

The formulation can be an infant feeding formula.

In another aspect, the invention features, a nutraceutical, which includes transgenically produced prolactin or transgenic preparation of prolactin, preferably human prolactin, and at least one nutritional component other than prolactin. The nutraceutical can be an infant feeding formula.

The transgenic prolactin or prolactin preparation can be made, e.g., by any method or organism described herein.

The transgenic prolactin or prolactin preparation can be, e.g., any described herein.

In another aspect, the invention features, a method of providing prolactin to a subject in need of prolactin. The method includes: administering transgenically produced prolactin or a transgenic preparation of prolactin to the subject.

In preferred embodiments the subject is: a person, e.g., a patient, in need of prolactin. E.g., the subject can be: a person in need of stimulation of lactation, e.g., a mother; a person in need of stimulation of the immune system, e.g., a person at risk for an immune disorder, e.g., a person at risk of an acquired immune disorder, e.g., Acquired Immunodeficiency Syndrome (AIDS), or a person infected with a human immunodeficiency virus (HIV); a person having a nutritional deficiency, e.g., a newborn having a nutritional deficiency; a person having an impairment in reproductive function; a newborn; or an infant.

The transgenic prolactin or prolactin preparation can be made, e.g., by any method or organism described herein.

The transgenic prolactin or prolactin preparation can be, e.g., any described herein.

In preferred embodiments the preparation is an infant feeding formula.

In any of the compositions and methods described herein, the transgenic prolactin preparation or formulations can be free of glycosylated prolactin. Glycosylated prolactin can be removed by methods known to those skilled in the art, e.g., by standard protein separation methods.

The expression of some transgenic proteins may result in an unwanted effect on the metabolism or health of the transgenic animal or its offspring.

Thus, in another aspect, the invention features a method of producing a transgenic protein in a transgenic animal (wherein the transgenic protein is one which exerts an effect on the metabolism of the transgenic animal) which includes:

expressing the transgenic protein, e.g., in the milk of the transgenic animal; and treating the transgenic animal to inhibit the effect of the transgenic protein on the transgenic animal.

For example, the animal can be administered, or the animal can transgenically express, a substance which inhibits the effect of the transgenic prolactin on the animal, e.g., a substance inhibits an activity of the transgenic prolactin. In preferred embodiments, the substance is a polypeptide. The substance can be, by way of example, an enzyme or a receptor, or a fragment thereof, or other molecule which interacts with or binds transgenic prolactin. It can act by competitive or non competitive inhibition of an activity of the transgenic prolactin, by altering the distribution or transport of the prolactin.

If the transgenic protein is found in a particular site in the transgenic animal, e.g., in a tissue, fluid, or organ, the substance can be administered to, or expressed at, that site. E.g., in the case of a transgenic protein which is expressed in the milk of a transgenic animal, the substance can be administered to, or expressed in, the milk of the transgenic animal.

In cases where the substance is transgenically expressed, the transgenic prolactin and the substance can be expressed from promoters of the same type, e.g., they can both be expressed from mammary specific promoters, e.g., milk specific promoters. The transgenic prolactin and the substance can be expressed from a promoter that results in equal expression of the two, or the two can be expressed from different promoters of different strength. This can result in greater or lesser expression of one or the other. In some cases it will be desirable for the expression of the substance, e.g., on a molar or weight basis, to exceed the expression of the transgenic prolactin. In other cases the opposite will optimize production of the substance. The substance can be expressed at a site other than the one where the prolactin is expressed. E.g., the substance can be administered to or expressed at a site in which the transgenic prolactin is unwanted, e.g., one into which the transgenic protein is likely to leak, e.g., blood. In preferred embodiments, the transgenic prolactin is expressed in the milk of the transgenic animal and the substance is administered to, or expressed in, the blood of the transgenic animal.

In preferred embodiments, an antibody which binds the transgenic prolactin is administered to or expressed in the transgenic animal. The antibody can be, by way of example, a single chain antibody or an intrabody. In preferred embodiments, the transgenic prolactin is expressed in milk and the antibody is expressed in the blood.

The substance can be administered to, or expressed as a second transgenic protein in, a transgenic animal. However, before producing a transgenic animal, e.g., a large transgenic animal, such as a transgenic goat, the effectiveness of the substance should be tested. This can be accomplished by administering, e.g., by injection, both the prolactin and the substance to an animal, e.g., a goat, and monitoring the effect of the prolactin on the metabolism or health of the transgenic animal. If the appropriate effect of the substance is seen, the transgenic animal can then be generated. It may be desirable to construct a transgenic animal which expresses transgenic prolactin, and to administer candidate substance to that animal in order to evaluate if substance is useful for creating a double transgenic animal, i.e., one which is transgenic for prolactin and for the substance.

Host health can also be optimized by tissue specific expression, e.g., expression in the mammary gland, preferably in the milk.

The structure of transgenic prolactin can be modified for such purposes as enhancing therapeutic or prophylactic efficacy, or stability (e.g., ex vivo shelf life and resistance to proteolytic degradation in vivo), or to optimize the health of the animal. Such modified prolactin, when designed to retain at least one activity of the natural prolactin, are considered functional equivalents of the prolactin described in more detail herein. Such modified peptide can be produced, for instance, by amino acid substitution, deletion, or addition.

In preferred embodiments, transgenic prolactin can be expressed as a transgenic fusion protein in which it is fused to a second polypeptide. Expression as a fusion protein can be used to optimize the health of the animal, isolation or recovery of the protein, or modify the ex vivo shelf life of the protein.

In preferred embodiments, the prolactin is expressed as a fusion protein with a second polypeptide sequence which fusion results in a minimization of an unwanted effect of the prolactin on the metabolism or health of the transgenic animal. The second polypeptide can be one which alters the activity of the prolactin of the fusion, e.g., by interfering with an interaction of the prolactin moiety with a second molecule, e.g., a receptor, e.g., a prolactin receptor. The second protein can be one which alters the tissue distribution of the fusion protein. E.g., the fusion of the second polypeptide to the prolactin moiety can prevent migration or transport of the fusion from the site of expression, e.g., mammary tissue or milk, to another site in the transgenic animal, e.g., the circulatory system or the blood.

In preferred embodiments, the second protein is cleaved from the prolactin moiety after the fusion protein is expressed or isolated.

The transgenic prolactin can be expressed as a fusion protein with a second polypeptide which optimizes the isolation or recovery of the transgenic prolactin. E.g., the second polypeptide can optimize isolation by: conferring a desired solubility property on the fusion protein, e.g., by making it more or less soluble; supplying a moiety which simplifies purification, e.g., by supplying an affinity moiety.

As used herein, the glycosylation of two proteins differ if they differ by one or more of the following parameters:

(1) the total molecular weight of sugar residues attached to the protein;

(2) the total number of sugar residues attached to the protein;

(3) the subunit composition of the attached sugar residues;

(4) the number of branch points present in the attached sugars;

(5) the location of branch points in the attached sugars;

(7) the number of sites at which sugars are attached to the protein;

(8) the position or positions, in the protein, where sugars are attached;

(10) the number of O-linked glycosylation sites; and

(11) the number of N-linked glycosylation sites.

Two preparations differ from one another if the proportion of transgenic prolactin molecules having a selected characteristic, e.g., one or more of those recited immediately above, differs from the proportion of molecules having that characteristic in the second preparation. For example, each of two preparations can contain glycosylated prolactin and non-glycosylated prolactin. The two preparations differ if, e.g., the proportion of non-glycosylated molecules differs between the preparations, e.g., if 50% of the molecules of the first preparation are non-glycosylated and only 10% of the molecules of the second preparation are non-glycosylated.

A preparation, as used herein, refers to a plurality of molecules produced by one or more transgenic animals. It can include molecules of differing glycosylation or it can be homogenous in this regard.

A purified preparation, substantially pure preparation of a polypeptide, or an isolated polypeptide as used herein, means, in the case of a transgenically produced polypeptide, a polypeptide that has been separated from at least one other protein, lipid, or nucleic acid with which it occurs in the transgenic animal or in a fluid, e.g., milk, or other substance, e.g., an egg, produced by the transgenic animal. The polypeptide is preferably separated from substances, e.g., antibodies or gel matrix, e.g., polyacrylamide, which are used to purify it. The polypeptide is preferably constitutes at least 10, 20, 50 70, 80 or 95% dry weight of the purified preparation. Preferably, the preparation contains: sufficient polypeptide to allow protein sequencing; at least 1, 10, or 100 μg of the polypeptide; at least 1, 10, or 100 mg of the polypeptide.

A substantially pure nucleic acid, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment Aproduced by PCR or restriction endonuclease treatment) independent of other DNA sequences. Substantially pure DNA also includes a recombinant DNA which is part of a hybrid gene encoding additional prolactin sequence.

Homology, or sequence identity, as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or have sequence identity at that position. The percent of homology or sequence identity between two sequences is a function of the number of matching or homologous positions shared by the two sequences divided by the number of positions compared ×100. For example, if 6 of 10, of the positions in two sequences are matched or homologous then the two sequences are 60% homologous or have 60% sequence identity. By way of example, the DNA sequences ATTGCC and TATGGC share 50% homology or sequence identity. Generally, a comparison is made when two sequences are aligned to give maximum homology or sequence identity.

The terms peptides, proteins, and polypeptides are used interchangeably herein.

As used herein, the term transgene means a nucleic acid sequence (encoding, e.g., one or more prolactin polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression and secretion of the selected nucleic acid encoding prolactin, e.g., in a mammary gland, all operably linked to the selected prolactin nucleic acid, and may include an enhancer sequence. The prolactin sequence can be operatively linked to a tissue specific promoter, e.g., mammary gland specific promoter sequence that results in the secretion of the protein in the milk of a transgenic mammal, a urine specific promoter, or an egg specific promoter.

As used herein, the term "transgenic cell" refers to a cell containing a transgene.

A transgenic organism, as used herein, refers to a transgenic animal or plant.

As used herein, a "transgenic animal" is a non-human animal in which one or more, and preferably essentially all, of the cells of the animal contain a heterologous nucleic acid introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

Mammals are defined herein as all animals, excluding humans, that have mammary glands and produce milk.

As used herein, a "dairy animal" refers to a milk producing animal. In preferred embodiments, the dairy animal produce large volumes of milk and have long lactating periods, e.g., cows or goats.

As used herein, the term "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "pharmaceutically acceptable composition" refers to compositions which comprise a therapeutically-effective amount of transgenic prolactin, formulated together with one or more pharmaceutically acceptable carrier(s).

As used herein, the term "formulation" refers to a composition in solid, e.g., powder, or liquid form, which includes a transgenic prolactin. Formulations can provide therapeutical or nutritional benefits. In preferred embodiments, formulations can include at least one nutritional component other than prolactin. These formulations may contain a preservative to prevent the growth of microorganisms.

As used herein, the term "nutraceutical," refers to a food substance or part of a food, which includes a transgenic prolactin. Nutraceuticals can provide medical or health benefits, including the prevention, treatment or cure of the disease. The transgenic protein will often be present in the nutraceutical at concentration of at least 1 mg/kg. A nutraceutical can include the milk of a transgenic animal. The nutraceutical can be an infant feeding formula.

As used herein, the term "prolactin" refers to a protein hormone naturally produced by anterior pituitary cells. Naturally-occurring human prolactin has a molecular weight of about 23 kDa and consists of approximately 198 amino acids. In preferred embodiments, prolactin has the amino acid sequence of a human prolactin.

A polypeptide has prolactin biological activity if it has one of the following properties: (1) it is active in the stimulation of breast development and milk production in a mammal; (2) it stimulates the immune system of a subject; (3) it influences reproductive function; (4) it inhibits, e.g., competitively or noncompetitively, binding of prolactin to a receptor, e.g., a prolactin receptor. A polypeptide has biological activity if it is an antagonist, agonist, or super-agonist of a polypeptide having one of the abovelisted properties.

As used herein, the language "subject" is intended to include human and nonhuman animals. In preferred embodiments, the subject is a person, e.g., a patient, in need of prolactin: E.g., a person in need of stimulation of lactation, e.g., a mother; a person in need of stimulation of the immune system, e.g., a person at risk for an immune disorder, e.g., a person at risk of an acquired immune disorder, e.g., Acquired Immunodeficiency Syndrome (AIDS), or a person infected with a hunan immunodeficiency virus (HIV); a person having a nutritional deficiency, e.g., a newborn having a nutritional deficiency; a person having an impairment in reproductive function; a newborn, or an infant. The term "non-human animals" of the invention includes all vertebrates, e.g., mammals and non-mammals, such as non-human primates, ruminants, birds, amphibians, reptiles. The application of transgenic technology to the commercial production of recombinant proteins in the milk of transgenic animals offers significant advantages over traditional methods of protein production. These advantages include a reduction in the total amount of required capital expenditures, elimination of the need for capital commitment to build facilities early in the product development life cycle, and lower direct production cost per unit for complex proteins. Of key importance is the likelihood that, for certain complex proteins, transgenic production may represent the only technologically and economically feasible method of commercial production.

Humans produce both glycosylated and non-glycosylated prolactin. Nonglycosylated prolactin is biologically active. Transgenic organisms, e.g., animals, are a preferred source of non-glycosylated prolactin. Infant feeding formulas which include transgenic prolactin, e.g., non-glycosylated prolactin, of the invention are particularly useful.

Other features and advantages of the invention will be apparent from the following detailed description, and from the claims.

DETAILED DESCRIPTION

Transzenic Mammals

Detailed methods for generating non-human transgenic animals are described herein and in the section entitled "Examples" below. DNA constructs can be introduced into the germ line of a mammal to make a transgenic mammal. For example, one or several copies of the construct may be incorporated into the genome of a mammalian embryo by standard transgenic techniques.

Any non-human mammal can be used in the methods described herein. It is often desirable to express the transgenic protein in the milk of transgenic animal. Mammals that produce large volumes of milk and have long lactating periods are preferred. Preferred mammals are ruminants, e.g., cows, sheep, camels or goats, e.g., Swiss origin goats, e.g., the Alpine, Saanen and Toggenburg breed goats. Additional examples of preferred animals include oxen, and pigs. Of course, each of these mammals may not be as effective as the others with respect to any given expression sequence of this invention. For example, a particular milk-specific promoter or signal sequence may be more effective in one mammal than in others. However, one of skill in the art may make such choices by following the teachings of this invention.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor.

Introduction of the prolactin transgene into the embryo may be accomplished by any means known in the art such as, for example, microinjection, electroporation, or lipofection. For example, the prolactin transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

The progeny of the transgenically manipulated embryos may be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals may be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity. The female species of these progeny will produce the desired protein in or along with their milk. Alternatively, the transgenic manmmals may be bred to produce other transgenic progeny usefull in producing the desired proteins in their milk.

Transgenic females may be tested for protein secretion into milk, using any of the assay techniques that are standard in the art (e.g., Western blots or enzymatic assays).

Production of Transgenic Protein in the Milk of a Transgenic Animal Milk Specific Promoters Useful transcriptional promoters are those promoters that are preferentially activated in mammary epithelial cells, including promoters that control the genes encoding milk proteins such as caseins, beta lactoglobulin (Clark et al., (1989) Bio/Technology-7: 487–492), whey acid protein (Gorton et al. (1987) BiolTechnology 5: 1183–1187), and lactalbumin (Soulier et al., (1992) FEBSLetts. 297:13). Casein promoters may be derived from the alpha, beta, gamma or kappa casein genes of any mammalian species; a preferred promoter is derived from the goat beta casein gene (DiTullio, (1992) BiolTechnology 10:74–77). Milk-specific protein promoter or the promoters that are specifically activated in mammary tissue can be derived from cDNA or genomic sequences. Preferably, they are genomic in origin.

DNA sequence information is available for all of the mammary gland specific genes listed above, in at least one, and often in several organisms. See, e.g., Richards et al., J Biol. Chem. 256, 526–532 (1981) (α-lactalbumin rat); Campbell et al., *Nucleic Acids Res.* 12, 8685–8697 (1984) (rat WAP); Jones et al., *J Biol. Chem.* 260, 7042–7050 (1985) (rat β-casein); Yu-Lee & Rosen, *J Biol. Chem.* 258, 10794–10804 (1983) (rat γ-casein); Hall, *Biochem. J* 242, 735–742 (1987) (α-lactalbumin human); Stewart, *Nucleic Acids Res.* 12, 389 (1984) (bovine αsl and κ casein cDNAs);

Gorodetsky et al., *Gene* 66, 87–96 (1988) (bovine β casein); Alexander et al., *Eur. J Biochem.* 178, 395–401 (1988) (bovine κ casein); Brignon et al., *FEBS Lett.* 188, 48–55 (1977) (bovine αS2 casein); Jamieson et al., *Gene* 61, 85–90 (1987), Ivanov et al., *Biol. Chem.* Hoppe-Seyler 369, 425–429 (1988), Alexander et al., *Nucleic Acids Res.* 17, 6739 (1989) (bovine β lactoglobulin); Vilotte et al., *Biochimie* 69, 609–620 (1987) (bovine α-lactalbumin). The structure and function of the various milk protein genes are reviewed by Mercier & Vilotte, *J Dairy Sci.* 76, 3079–3098 (1993) (incorporated by reference in its entirety for all purposes). If additional flanking sequence are useful in optimizing expression, such sequences can be cloned using the existing sequences as probes. Mammary-gland specific regulatory sequences from different organisms can be obtained by screening libraries from such organisms using known cognate nucleotide sequences, or antibodies to cognate proteins as probes.

Signal Sequences

Useful signal sequences are milk-specific signal sequences or other signal sequences which result in the secretion of eukaryotic or prokaryotic proteins. Preferably, the signal sequence is selected from milk-specific signal sequences, i.e., it is from a gene which encodes a product secreted into milk. Most preferably, the milk-specific signal sequence is related to the milk-specific promoter used in the expression system of this invention. The size of the signal sequence is not critical for this invention. All that is required is that the sequence be of a sufficient size to effect secretion of the desired recombinant protein, e.g., in the mammary tissue. For example, signal sequences from genes coding for caseins, e.g., alpha, beta, gamma or kappa caseins, beta lactoglobulin, whey acid protein, and lactalbumin are useful in the present invention. The preferred signal sequence is the goat β-casein signal sequence.

Signal sequences from other secreted proteins, e.g., proteins secreted by liver cells, kidney cell, or pancreatic cells can also be used.

Amino-Terminal Regions of Secreted Proteins

The efficacy with which a non-secreted protein is secreted can be enhanced by inclusion in the protein to be secreted all or part of the coding sequence of a protein which is normally secreted. Preferably the entire sequence of the protein which is normally secreted is not included in the sequence of the protein but rather only a portion of the amino terminal end of the protein which is normally secreted. For example, a protein which is not normally secreted is fused (usually at its amino terminal end) to an amino terminal portion of a protein which is normally secreted.

Preferably, the protein which is normally secreted is a protein which is normally secreted in milk. Such proteins include proteins secreted by mammary epithelial cells, milk proteins such as caseins, beta lactoglobulin, whey acid protein, and lactalbumin. Casein proteins include alpha, beta, gamma or kappa casein genes of any mammalian species. A preferred protein is beta casein, e.g., goat beta casein. The sequences which encode the secreted protein can be derived from either CDNA or genomic sequences. Preferably, they are genomic in origin, and include one or more introns.

DNA Constructs

The prolactin can be expressed from a construct which includes a promoter specific for marnmary epithelial cells, e.g., a casein promoter, e.g., a goat beta casein promoter, a milk-specific signal sequence, e.g., a casein signal sequence, e.g., a β-casein signal sequence, and a DNA encoding prolactin.

An expression system or construct described herein can also include a 3' untranslated region downstream of the DNA sequence coding for the non-secreted protein. Such regions can stabilize the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the casein 3' untranslated region or other 3' untranslated sequences well known in the art. Preferably, the 3' untranslated region is derived from a milk specific protein. The length of the 3' untranslated region is not critical but the stabilizing effect of its poly A transcript appears important in stabilizing the RNA of the expression sequence.

Optionally, the expression system or construct includes a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they appear to be useful in improving the level of expression.

The construct can also include about 10%, 20%, 30%, or more of the N-terminal coding region of a gene preferentially expressed in mammary epithelial cells. For example, the N-terminal coding region can correspond to the promoter used, e.g., a goat β-casein N-terminal coding region.

Expression systems can be prepared using methods known in the art. An expression system can be prepared as part of a larger plasmid. Such preparation allows the cloning and selection of the correct constructions in an efficient manner as is known in the art. Expression systems can be located between convenient restriction sites on the plasmid so that they can be easily isolated from the remaining plasmid sequences for incorporation into the desired mammal.

Prior art methods often include making a construct and testing it for the ability to produce a product in cultured cells prior to placing the construct in a transgenic animal. Surprisingly, the inventors have found that such a protocol may not be of predictive value in determining if a normally non-secreted protein can be secreted, e.g., in the milk of a transgenic animal. Therefore, it may be desirable to test constructs directly in transgenic animals, e.g., transgenic mice, as some constructs which fail to be secreted in CHO cells are secreted into the milk of transgenic animals.

Pharmaceutical Compositions

A transgenically produced polypeptide or preparation of the invention can be incorporated into pharmaceutical compositions useful to attenuate, inhibit, or prevent a disease or a disorder, e.g., an immune or a reproductive disorder, or to ameliorate a deficiency in a subject, e.g., a nutritional deficiency or a deficiency in lactation. The compositions should contain a therapeutic or prophylactic amount of the transgenically produced prolactin, in a pharmaceutically-acceptable carrier or in the milk of the transgenic animal.

The pharmaceutical carrier can be any compatible, non-toxic substance suitable to deliver the polypeptides to the patient. Sterile water, alcohol, fats, waxes, and inert solids may be used as the carrier. Pharnaceutically-acceptable adjuvants, buffering agents, dispersing agents, and the like, may also be incorporated into the pharmaceutical compositions. The concentration of the transgenically produced peptide or other active agent in the pharmaceutical composition can vary widely, i.e., from less than about 0.1% by weight, usually being at least about 1% weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

For nasal administration, the polypeptides can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273–313; and Raeburn et al. (1992) *J. Pharmacol. Toxicol. Methods* 27:143–159.

The pharmaceutical compositions of the present invention can be administered intravenously or orally. Intradermal or intramuscular administration is also possible in some circumstances. The compositions can be administered for prophylactic treatment of individuals suffering from, or at risk of a disease or a disorder, e.g., an HIV-infected person. For therapeutic applications, the pharmaceutical compositions are administered to a subject suffering from a disease or disorders, e.g., an immune or reproductive disorder, or a subject having a nutritional deficiency, in an amount sufficient to inhibit, prevent, or ameliorate the disease, or a nutritional or lactational deficiency. An amount adequate to accomplish this is defined as a "therapeutically-effective dose".

Formulations

A formulation includes transgenically produced prolactin. In preferred embodiments, the formulation includes transgenic prolactin, and at least one nutritional component other than prolactin. Nutritional component can be: a protein, e.g., a milk protein; a vitamin, e.g., vitamin A, vitamin B, vitamin D; a carbohydrate; a mineral, e.g., calcium, phosphorous, iron. The formulation may be in solid or liquid form. In preferred embodiments, the formulation further includes a liquid carrier, e.g., a diluent, e.g., water.

In preferred embodiments, these formulations are suitable for oral, topical or intravenous or intramuscular administration to a subject. Formulations are useful for therapeutic and/or nutritional applications.

Nutraceuticals

A transgenic prolactin can be included in a nutraceutical. Preferably, the food is milk or milk product obtained from the transgenic mammal which expresses the transgenic protein of the invention. Examples of other nutraceuticals include but are not limited to desserts, ice creams, puddings, and jellies which incorporate the transgenic protein of the invention, as well as soups and beverages. In addition, the isolated transgenic protein of the invention can be provided in powder or tablet form, with or without other known additives, carriers, fillers and diluents. Nutraceuticals are described in Scott Hegenhart, Food Product Design, Dec. 1993. The nutraceutical can be an infant feeding formula.

Transgenic Plants

The transgenic organisms can be a transgenic plant in which the DNA transgene is inserted into the nuclear or plastidic genome. The plant transformation is known as the art. See, in general, *Methods in Enzymology* Vol. 153 ("Recombinant DNA Part D") 1987, Wu and Grossman Eds., Academic Press and European Patent Application EP 693554.

Foreign nucleic acid is can be mechanically transferred by microinjection directly into plant cells by use of micropipettes. Foreign nucleic acid can be transferred into a plant cell by using polyethylene glycol which forms a precipitation complex with the genetic material that is taken up by the cell (Paszkowski et al. (1984) *EMBO J.* 3:2712–22).

Foreign nucleic acid can be introduced into a plant cell by electroporation (Fromm et al. (1985) *Proc. Natl. Acad Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can also be used as a vector for introducing foreign nucleic acid into plant cells (Hohn et al. (1982) "Molecular Biology of Plant Tumors," Academic Press, New York, pp. 549–560; Howell, U.S. Pat. No. 4,407,956).

CaMV viral DNA genome is inserted into a parent bacterial plasmid creating a recombinant DNA molecule which can be propagated in bacteria. After cloning, the recombinant plasmid again can be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of foreign nucleic acid into plant cells is high velocity ballistic penetration by small particles with the nucleic acid either within the matrix of small beads or particles, or on the surface (Klein et al. (1987) *Nature* 327:70–73). Although typically only a single introduction of a new nucleic acid segment is required, this method particularly provides for multiple introductions.

A preferred method of introducing the nucleic acids into plant cells is to infect a plant cell, an explant, a meristem or a seed with *Agrobacterium tumefaciens* transformed with the nucleic acid. Under appropriate conditions known in the art, the transformed plant cells are grown to form shoots, roots, and develop further into plants. The nucleic acids can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," Science 233:496–498; Fraley et al. (1983) *Proc. Natl. Acad. Sci. USA* 80:4803).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without affecting its transferring ability. By removing the tumor-causing genes so that they no longer interfere, the modified Ti plasmid can then be used as a vector for the transfer of the gene constructs of the invention into an appropriate plant cell.

There are presently at least three different ways to transform plant cells with Agrobacterium: (1) co-cultivation of Agrobacterium with cultured isolated protoplasts; (2) transformation of cells or tissues with Agrobacterium; or (3) transformation of seeds, apices or meristems with Agrobacterium. The first method requires an established culture system that allows culturing protoplasts and plant regeneration from cultured protoplasts. The second method requires that the plant cells or tissues can be transformed by Agrobacterium and that the transformed cells or tissues can be induced to regenerate into whole plants. The third method requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and can be used in this invention.

Plants from which protoplasts can be isolated and cultured to give whole regenerated plants can be transformed so that whole plants are recovered which contain the transferred foreign gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

Many plants can be regenerated from cultured cells or tissues. The term "regeneration" as used herein, means growing a whole plant from a plant cell, a group of plant cells, a plant part or a plant piece (e.g. from a protoplast, callus, or tissue part) (*Methods in Enzymology* Vol. 153 ("Recombinant DNA Part D") 1987, Wu and Grossman Eds., Academic Press; also *Methods in Enzymology*, Vol. 118; and KIee et al., (1987) *Annual Review of Plant Physiology,* 38:467–486).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," *Protoplasts* (1983)-Lecture Proceedings, pp. 12–29, (Birkhauser, Basal 1983); P. J. Dale, "Protoplast Culture and Plant Regeneration of Cereals and Other Recalcitrant Crops," *Protoplasts* (1983)-Lecture Proceedings, pp. 31–41, (Birkhauser, Basel 1983); and H. Binding, "Regeneration of Plants," *Plant Protoplasts*, pp. 21–73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants are propagated by the taking of cuttings or by tissue culture techniques to produce multiple identical plants for trialling, such as testing for production characteristics. Selection of a desirable transgenic plant is made and new varieties are obtained thereby, and propagated vegetatively for commercial sale. In seed propagated crops, the mature transgenic plants are self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method a selected inbred line is crossed with another inbred line to produce the hybrid.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

However, any additional attached vector sequences which confers resistance to degradation of the nucleic acid fragment to be introduced, which assists in the process of genomic integration or provides a means to easily select for those cells or plants which are transformed are advantageous and greatly decrease the difficulty of selecting useable transgenic plants or plant cells.

Selection of transgenic plants or plant cells is typically based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy, see, Harborne et al. (Eds.), (1975) *The Flavonoids*, Vols. 1 and 2, [Acad. Press]). Appropriate plants are selected and further evaluated. Methods for generation of genetically engineered plants are further described in U.S. Pat. No. 5,283,184, U.S. Pat. No. 5,482,852, and European Patent Application EP 693 554.

Fragments and Analogs of Prolactin

The transgenically produced prolactin can have the amino acid sequence of a naturally occurring protein or it can be a fragment or analog of a naturally occurring protein.

In a preferred embodiment, the prolactin polypeptide differs in amino acid sequence at up to 1, 2, 3, 5, or 10 residues, from the sequence of naturally occurring prolactin. In other preferred embodiments, the prolactin polypeptide differs in amino acid sequence at up to 1, 2, 3, 5, or 10% of the residues from a sequence of naturally occurring prolactin. In preferred embodiments, the differences are such that the prolactin polypeptide exhibits an prolactin biological activity. In other preferred embodiments, the differences are such that the prolactin polypeptide does not have prolactin biological activity. In preferred embodiments, one or more, or all of the differences are conservative amino acid changes. In other preferred embodiments, one or more, or all of the differences are other than conservative amino acid changes.

In preferred embodiments, the prolactin polypeptide is a fragment of a full length prolactin polypeptide, e.g., a firagment of a naturally occurring prolactin polypeptide.

In preferred embodiments: the fragment is at least 5, 10, 20, 50, 100, or 150 amino acids in length; the fragment is equal to or less than 200, 150, 100, 50 amino acid residues in length; the fragment has a biological activity of a naturally occurring prolactin; the fragment is either, an agonist or an antagonist, of a biological activity of a naturally occurring prolactin; the fragment can inhibit, e.g., competitively or non competitively inhibit, the binding of prolactin to a receptor, or an enzyme.

In preferred embodiments, the fragment it has at least 60, and more preferably at least 70, 80, 90, 95, 99, or 100% sequence identity with the corresponding amino acid sequence of naturally occurring prolactin.

In preferred embodiments, the fragment is a fragment of a vertebrate, e.g., a mammalian, e.g. a primate, e.g., a human prolactin polypeptide.

In a preferred embodiment, the fragment differs in amino acid sequence at up to 1, 2, 3, 5, or 10 residues, from the corresponding residues of naturally occurring prolactin. In other preferred embodiments, the fragment differs in amino acid sequence at up to 1, 2, 3, 5, or 10% of the residues from the corresponding residues of naturally occurring prolactin. In preferred embodiments, the differences are such that the fragment exhibits a prolactin biological activity. In other preferred embodiments the differences are such that the fragment does not have prolactin biological activity. In preferred embodiments, one or more, or all of the differences are conservative amino acid changes. In other preferred embodiments one or more, or all of the differences are other than conservative amino acid changes.

Polypeptides of the invention include those which arise as a result of the existence of multiple genes, alternative transcription events, alternative RNA splicing events, and alternative translational and postranslational events.

Production of Fragments and Analogs

One skilled in the art can alter the disclosed structure of prolactin by producing fragments or analogs, and test the newly produced structures for activity. Examples of prior art methods which allow the production and testing of fragments and analogs are discussed below. These, or other methods, can be used to make and screen fragments and analogs of a prolactin polypeptide. In preferred embodiments, the prolactin structure modified is human prolactin.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter fuinction, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating finctional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the singlestranded DNA template molecule. The oligonucleotides are readily synthesized using techniques known in the art such as that described by Crea et al. (*Proc. Natl. Acad Sci.* USA, 75: 5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Petptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, the interaction, e.g., binding of prolactin to a prolactin-interacting polypeptide, e.g., prolactin receptor, or the interaction, e.g., binding of a candidate polypeptide with a prolactin polypeptide facilitate relatively easy isolation of the vector encoding the gene whose product was detected. Each of the techniques described below is amenable to high through-put analysis for screening large numbers of sequences created, e.g., by random mutagenesis techniques.

Two Hybrid Systems Two hybrid assays such as the system described above (as with the other screening methods described herein), can be used to identify fragments or analogs of a prolactin polypeptide which binds to a prolactin interactor. These may include agonists, superagonists, and antagonists.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially finctional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992)*J Biol. Chem.* 267:16007–16010; Criffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J Bacteriol.* 174, 4239–4245 and Klauser et al. (1990) *EMBO J* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein Lacd to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a Laci-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. USA.* 89–1869) This scheme, sometimes referred to as peptides-on-plasmids, differs in two important ways from the phage display methods. First, the peptides are attached to the C-terminus of the fusion protein, resulting in the display of the library members as peptides having free carhoxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. USA.* 87, 6378–6382) A second difference is the set of biological biases affecting the population of peptides actually present in the libraries. The Lacd fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the Lacd and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J Med Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

This invention is further illustrated by the following examples which in no way should be construed as being further limiting. The contents of all cited references (including literature references, issued patents, published patent applications, and copending patent applications) cited throughout this application are hereby expressly incorporated by reference.

EXAMPLES

Generation of a Prolactin Construct cDNA encoding human prolactin can be introduced in the BC355 vector containing the regulatory elements of the goat beta-casein gene, creating a transgene having the prolactin sequence under the control of a milk specific promoter. This construct can be used to target human prolactin expression to the lactating mammary gland of a transgenic mammal.

Testing and Characterization of Gene Constructs in Transgenic Mice

Transgene constructs are generally tested in a mouse model system to assess their ability to direct high levels of expression and their ability to express in a tissuespecific manner.

Transgenic mice are generated by microinjecting mouse embryos with DNA fragments of interest. Western analysis of the milk of the prolactin transgenic mice can be performed using monoclonal anti-prolactin antibodies to determine which animals express prolactin protein in the milk.

Generation and Characterization of Transgenic Goats

A founder ($F_o$) transgenic goat can be made by transfer of fertilized goat eggs that have been microinjected with a construct (e.g., a BC355 vector containing the human prolactin gene operably linked to the regulatory elements of the goat beta-casein gene). The methodologies that follow in this section can be used to generate transgenic goats.

Goat Species and breeds

Swiss origin goats, e.g., the Alpine, Saanen, and Toggenburg breeds, are useful in the production of transgenic goats.

The sections outlined below briefly describe the steps required in the production of transgenic goats. These steps include superovulation of female goats, mating to fertile males and collection of fertilized embryos. Once collected, pronuclei of one-cell fertilized embryos are microinjected with DNA constructs. All embryos from one donor female are kept together and transferred to a single recipient female if possible.

Goat superovulation

The timing of estrus in the donors is synchronized on Day 0 by 6 mg subcutaneous norgestomet ear implants (Syncromate-B, CEVA Laboratories, Inc., Overland Park, Kans.). Prostaglandin is administered after the first seven to nine days to shut down the endogenous synthesis of progesterone. Starting on Day 13 after insertion of the implant, a total of 18 mg of follicle-stimulating hormone (FSH - Schering Corp., Kenilworth, N.J.) is given intramuscularly over three days in twice-daily injections. The implant is removed on Day 14. Twenty-four hours following implant removal the donor animals are mated several times to fertile males over a two-day period (Selgrath, et al., Theriogenology, 1990. pp. 1195–1205).

Embryo collection

Surgery for embryo collection occurs on the second day following breeding (or 72 hours following implant removal). Superovulated does are removed from food and water 36 hours prior to surgery. Does are administered 0.8 mg/kg Diazepam (Valium®), IV, followed immediately by 5.0 mg/kg Ketamine (Keteset), IV. Halothane (2.5%) is administered during surgery in 2 L/min oxygen via an endotracheal tube. The reproductive tract is exteriorized through a midline laparotomy incision. Corpora lutea, unruptured follicles greater than 6 mm in diameter, and ovarian cysts are counted to evaluate superovulation results and to predict the number of embryos that should be collected by oviductal flushing. A cannula is placed in the ostium of the oviduct and held in place with a single temporary ligature of 3.0 Prolene. A 20 gauge needle is placed in the uterus approximately 0.5 cm from the uterotubal junction. Ten to twenty ml of sterile phosphate buffered saline (PBS) is flushed through the cannulated oviduct and collected in a Petri dish. This procedure is repeated on the opposite side and then the reproductive tract is replaced in the abdomen. Before closure, 10–20 ml of a sterile saline glycerol solution is poured into the abdominal cavity to prevent adhesions. The linea alba is closed with simple interrupted sutures of 2.0 Polydioxanone or Supramid and the skin closed with sterile wound clips.

Fertilized goat eggs are collected from the PBS oviductal flushings on a stereomicroscope, and are then washed in Ham's F12 medium (Sigma, St. Louis, Mo.) containing 10% fetal bovine serum (FBS) purchased from Sigma. In cases where the pronuclei are visible, the embryos is immediately microinjected. If pronuclei are not visible, the embryos are placed in Ham's F12 containing 10% FBS for short term culture at 37° C. in a humidified gas chamber containing 5% CO2 in air until the pronuclei become visible (Selgrath, et al., Theriogenology, 1990. pp. 1195–1205).

Microinjection procedure

One-cell goat embryos are placed in a microdrop of medium under oil on a glass depression slide. Fertilized eggs having two visible pronuclei are immobilized on a flame-polished holding micropipet on a Zeiss upright microscope with a fixed stage using Normarski optics. A pronucleus is. microinjected with the DNA construct of interest, e.g., a BC355 vector containrng the human prolactin gene operably linked to the regulatory elements of the goat beta-casein gene, in injection buffer (Tris-EDTA) using a fine glass microneedle (Selgrath, et al., Theriogenology, 1990. pp. 1195–1205).

Embryo development

After microinjection, the surviving embryos are placed in a culture of Ham's F12 containing 10% FBS and then incubated in a humidified gas chamber containing 5% CO2 in air at 37° C. until the recipient animals are prepared for embryo transfer (Selgrath, et al., Theriogenology, 1990. p. 1195–1205).

Preparation of recipients

Estrus synchronization in recipient animals is induced by 6 mg norgestomet ear implants (Syncromate-B). On Day 13 after insertion of the implant, the animals are given a single non-superovulatory injection (400 I.U.) of pregnant mares serum gonadotropin (PMSG) obtained from Sigma. Recipient females are mated to vasectomized males to ensure estrus synchrony (Selgrath, et al., Theriogenology, 1990. pp. 1195–1205).

Embryo Transfer

All embryos from one donor female are kept together and transferred to a single recipient when possible. The surgical procedure is identical to that outlined for embryo collection outlined above, except that the oviduct is not cannulated, and the embryos are transferred in a minimal volume of Ham's F12 containing 10% FBS into the oviductal lumen via the fimbria using a glass micropipet. Animals having more than six to eight ovulation points on the ovary are deemed unsuitable as recipients. Incision closure and post-operative care are the same as for donor animals (see, e.g., Selgrath, et al., Theriogenology, 1990. pp. 1195–1205).

Monitoring of pregnancy and parturition

Pregnancy is determined by ultrasonography 45 days after the first day of standing estrus. At Day 110 a second ultrasound exam is conducted to confirm pregnancy and assess fetal stress. At Day 130 the pregnant recipient doe is vaccinated with tetanus toxoid and Clostridium C&D. Selenium and vitamin E (Bo-Se) are given IM and Ivermectin was given SC. The does are moved to a clean stall on Day 145 and allowed to acclimatize to this environment prior to inducing labor on about Day 147. Parturition is induced at Day 147 with 40 mg of PGF2a (Lutalyse®, Upjohn Company, Kalamazoo Mich.). This injection is given IM in two doses, one 20 mg dose followed by a 20 mg dose four hours later. The doe is under periodic observation during the day and evening following the first injection of Lutalyse® on Day 147. Observations are increased to every 30 minutes beginning on the morning of the second day. Parturition occurred between 30 and 40 hours after the first injection. Following delivery the doe is milked to collect the colostrum and passage of the placenta is confirmed.

Verification of the transgenic nature of $F_0$ animals

To screen for transgenic $F_0$ animals, genomic DNA is isolated from two different cell lines to avoid missing any mosaic transgenics. A mosaic animal is defined as any goat that does not have at least one copy of the trnnsgene in every cell. Therefore, an ear tissue sample (mesoderm) and blood sample are taken from a two day old $F_0$ animal for the isolation of genomic DNA (Lacy, et al., A Laboratory Manual, 1986, Cold Springs Harbor, N.Y.; and Herrmann and Frischauf, Methods Enzymology, 1987. 152: pp. 180–183). The DNA samples are analyzed by the polymerase chain reaction (Gould, et al., Proc. Natl. Acad. Sci, 1989. 86: pp. 1934–1938) using primers specific for human prolactin gene and by Southern blot analysis (Thomas, Proc Natl. Acad. Sci., 1980. 77:5201–5205) using a random primed human prolactin cDNA probe (Feinberg and Vogelstein, Anal. Bioc., 1983. 132: pp. 6–13). Assay sensitivity is estimated to be the detection of one copy of the transgene in 10% of the somatic cells.

Generation and Selection of production herd

The procedures described above can be used for production of transgenic founder ($F_0$) goats, as well as other transgenic goats. The transgenic $F_0$ founder goats, for example, are bred to produce milk, if female, or to produce a transgenic female offspring if it is a male founder. This transgenic founder male, can be bred to non-transgenic females, to produce transgenic female offspring.

Transmission of transgene and pertinent characteristics

Transmission of the transgene of interest, in the goat line is analyzed in ear tissue and blood by PCR and Southern blot analysis. For example, Southern blot analysis of the founder male and the three transgenic offspring shows no rearrangement or change in the copy number between generations. The Southern blots are probed with human prolactin cDNA probe. The blots are analyzed on a Betascope 603 and copy number determined by comparison of the transgene to the goat beta casein endogenous gene.

Evaluation of expression levels

The expression level of the transgenic protein, in the milk of transgenic animals, is determined using enzymatic assays or Western blots.

Purification from milk

The transgenic protein can be produced in milk at relatively high concentrations and in large volumes, providing continuous high level output of normally processed peptide that is easily harvested from a renewable resource. There are several different methods known in the art for isolation of proteins form milk.

Milk proteins usually are isolated by a combination of processes. Raw milk first is fractionated to remove fats, for example, by skimming, centrifugation, sedimentation (H.E. Swaisgood, Developments in Dairy Chemistry, I: Chemistry of Milk Protein, Applied Science Publishers, NY, 1982), acid precipitation (U.S. Pat. No. 4,644,056) or enzymatic coagulation with rennin or chymotrypsin (Swaisgood, ibid.). Next, the major milk proteins may be fractionated into either a clear solution or a bulk precipitate from which the specific protein of interest may be readily purified.

French Patent No. 2487642 describes the isolation of milk proteins from skim milk or whey by membrane ultrafiltration in combination with exclusion chromatography or ion exchange chromatography. Whey is first produced by removing the casein by coagulation with rennet or lactic acid. U.S. Pat. No. 4,485,040 describes the isolation of an alpha-lactoglobulin-enriched product in the retentate from whey by two sequential ultrafiltration steps. U.S. Pat. No. 4,644,056 provides a method for purifying immunoglobulin from milk or colostrum by acid precipitation at pH 4.0–5.5, and sequential cross-flow filtration first on a membrane with 0.1 –1.2 micrometer pore size to clarify the product pool and then on a membrane with a separation limit of 5–80 kd to concentrate it.

Similarly, U.S. Pat. No. 4,897,465 teaches the concentration and enrichment of a protein such as immunoglobulin from blood serum, egg yolks or whey by sequential ultrafiltration on metallic oxide membranes with a pH shift. Filtration is carried out first at a pH below the isoelectric point (pI) of the selected protein to remove bulk contaminants from the protein retentate, and next at a pH above the pl of the selected protein to retain impurities and pass the selected protein to the permeate. A different filtration concentration method is taught by European Patent No. EP 467 482 B 1 in which defatted skim milk is reduced to pH 3–4, below the pl of the milk proteins, to solubilize both casein and whey proteins. Three successive rounds of ultrafiltration or diafiltration then concentrate the proteins to form a retentate containing 15–20% solids of which 90% is protein. Alternatively, British Patent Application No. 2179947 discloses the isolation of lactoferrin from whey by ultrafiltration to concentrate the sample, followed by weak cation exchange chromatography at approximately a neutral pH. No measure of purity is reported. In PCT Publication No. WO 95/22258, a protein such as -lactoferrin is recovered from milk that has been adjusted to high ionic strength by the addition of concentrated salt, followed by cation exchange chromatography.

In all of these methods, milk or a fraction thereof is first treated to remove fats, lipids, and other particulate matter that would foul filtration membranes or chromatography media. The initial fractions thus produced may consist of casein, whey, or total milk protein, from which the protein of interest is then isolated.

PCT Patent Publication No. WO 94/19935 discloses a method of isolating a biologically active protein from whole milk by stabilizing the solubility of total milk proteins with a positively charged agent such as arginine, imidazole or Bis-Tris. This treatment forms a clarified solution from which the protein may be isolated, e.g., by filtration through membranes that otherwise would become clogged by precipitated proteins.

USSN 08/648,235 discloses a method for isolating a soluble milk component, such as a peptide, in its biologically active form from whole milk or a milk fraction by tangential flow filtration. Unlike previous isolation methods, this eliminates the need for a first fractionation of whole milk to remove fat and casein micelles, thereby simplifying the process and avoiding losses of recovery and bioactivity. This method may be used in combination with additional purification steps to further remove contaminants and purify the component of interest.

The Sequence of Prolactin

The sequence of prolactin is known in the art. The sequence of human prolactin can be found in Truong et al., 1984, *EMBO Journal* 3:429–437.

Other Transgenic Animals

Prolactin can be expressed from a variety of transgenic animals. A protocol for the production of a transgenic pig can be found in White and Yannoutsos, *Current Topics in Complement Research: 64th Forum in Immunology*, pp. 88–94; U.S. Pat. No. 5,523,226; U.S. Pat. No. 5,573,933; PCT Application WO93/25071; and PCT Application WO95/04744. A protocol for the production of a transgenic mouse can be found in U.S. Pat. No. 5,530,177. A protocol for the production of a transgenic rat can be found in Bader and Ganten, Clinical and Experimental Pharmacology and Physiology, Supp. 3:S81–S87, 1996. A protocol for the production of a transgenic cow can be found in *Transgenic Animal Technology, A Handbook,* 1994, ed., Carl A. Pinkert, Academic Press, Inc. A protocol for the production of a transgenic sheep can be found in *Transgenic Animal Technology, A Handbook,* 1994, ed., Carl A. Pinkert, Academic Press, Inc.

All patents and other references cited herein are hereby incorporated by reference.

Other embodiments are within the following claims.

What is claimed is:

1. A milk preparation obtained from a transgenic mammal whose genome contains a transgene wherein said transgene comprises a polynucleotide encoding a prolactin protein operably linked to a mammary gland specific promoter, wherein said prolactin protein is expressed in the mammary epithelial cells of said transgenic mammal and wherein less than 20% of the prolactin molecules in the milk preparation of the transgenic mammal are glycosylated.

2. The milk preparation of claim 1, wherein less than 10% of the prolactin molecules in the milk preparation of the transgenic mammal are glycosylated.

3. The milk preparation of claim 1, wherein less than 5% of the prolactin molecules in the milk preparation of the transgenic mammal are glycosylated.

4. The milk preparation of claim 1, wherein the prolactin is human prolactin.

5. The milk preparation of claim 1, wherein the transgenic mammal is a goat.

6. The milk preparation of claim 1, wherein the milk preparation comprises at least 1 mg/ml prolactin.

* * * * *

UNITED STATES PATENT AND TRADEMARK OFFICE
CERTIFICATE OF CORRECTION

PATENT NO.    : 6,210,736 B1                                              Page 1 of 1
DATED         : April 3, 2001
INVENTOR(S)   : Brian Wilburn and Yann Echelard It is certified that error appears in the above-identified patent and that said Letters Patent is hereby corrected as shown below:

<u>Title page,</u>
Please insert under Related Foreign Application Data;
-- PCT Application No. PCT/US97/10489, filed on June 17, 1997. --

Signed and Sealed this

Fourth Day of February, 2003

JAMES E. ROGAN
*Director of the United States Patent and Trademark Office*